(12) United States Patent
Albert et al.

(10) Patent No.: US 8,509,882 B2
(45) Date of Patent: Aug. 13, 2013

(54) HEART MONITORING SYSTEM USABLE WITH A SMARTPHONE OR COMPUTER

(75) Inventors: David Albert, Oklahoma City, OK (US); Bruce Richard Satchwell, Carrara (AU); Kim Norman Barnett, Mt. Tamborine (AU)

(73) Assignee: AliveCor, Inc., San Francisco, CA (US)

( * ) Notice: Subject to any disclaimer, the term of this patent is extended or adjusted under 35 U.S.C. 154(b) by 245 days.

(21) Appl. No.: 12/796,188

(22) Filed: Jun. 8, 2010

(65) Prior Publication Data

US 2011/0301435 A1  Dec. 8, 2011

(51) Int. Cl.
*A61B 5/04* (2006.01)
(52) U.S. Cl.
USPC .......................................................... 600/509
(58) Field of Classification Search
None
See application file for complete search history.

(56) References Cited

U.S. PATENT DOCUMENTS

| | | | |
|---|---|---|---|
| 3,717,857 A | 2/1973 | Evans | |
| 3,731,311 A | 5/1973 | Williams | |
| 3,768,014 A | 10/1973 | Smith et al. | |
| 3,779,237 A * | 12/1973 | Goeltz et al. | 600/515 |
| 3,782,367 A | 1/1974 | Hochberg et al. | |
| 3,882,277 A | 5/1975 | DePedro et al. | |
| 3,885,552 A | 5/1975 | Kennedy | |
| 3,898,984 A | 8/1975 | Mandel et al. | |
| 3,909,599 A | 9/1975 | Trott, Jr. et al. | |
| 4,027,146 A | 5/1977 | Gilmore | |
| 4,083,366 A | 4/1978 | Gombrich et al. | |
| 4,095,050 A | 6/1978 | Beachem et al. | |
| 4,250,888 A | 2/1981 | Grosskopf | |
| 4,281,664 A | 8/1981 | Duggan | |
| 4,409,984 A | 10/1983 | Dick | |
| 4,531,527 A | 7/1985 | Reinhold, Jr. et al. | |
| 4,567,883 A | 2/1986 | Langer et al. | |
| 4,803,625 A | 2/1989 | Fu et al. | |
| 4,938,229 A | 7/1990 | Bergelson et al. | |
| 4,981,141 A | 1/1991 | Segalowitz | |
| 5,023,906 A | 6/1991 | Novas | |
| 5,191,891 A | 3/1993 | Righter | |
| 5,218,969 A | 6/1993 | Bredesen et al. | |
| 5,301,679 A | 4/1994 | Taylor | |

(Continued)

FOREIGN PATENT DOCUMENTS

| | | |
|---|---|---|
| CH | 675675 | 4/1992 |
| GB | 2181554 | 4/1987 |

(Continued)

OTHER PUBLICATIONS

"Readmyheart Personal Handheld ECG Monitor with Free Illustrator Book & Free Electrodes V2.2"; printed from website http://www.amazon.com/Readmyheart-Personal-Handheld-illustrator-Electrodes/dp/B0010AN63W; printed on Mar. 26, 2010; 4 pages.

(Continued)

*Primary Examiner* — Christopher D Koharski
*Assistant Examiner* — Elizabeth K So
(74) *Attorney, Agent, or Firm* — Shay Glenn LLP

(57) ABSTRACT

A personal monitoring device has a sensor assembly configured to sense physiological signals upon contact with a user's skin. The sensor assembly produces electrical signals representing the sensed physiological signals. A converter assembly, integrated with, and electrically connected to the sensor assembly, converts the electrical signals generated by the sensor assembly to a frequency modulated physiological audio signal having a carrier frequency in the range of from about 6 kHz to about 20 kHz.

13 Claims, 4 Drawing Sheets

(56) References Cited

U.S. PATENT DOCUMENTS

| | | | |
|---|---|---|---|
| 5,321,618 A | 6/1994 | Gressman |
| 5,333,616 A | 8/1994 | Mills et al. |
| 5,336,245 A | 8/1994 | Adams et al. |
| 5,337,752 A | 8/1994 | Reeves |
| 5,339,824 A | 8/1994 | Engira |
| 5,365,935 A | 11/1994 | Righter et al. |
| 5,433,736 A | 7/1995 | Nilsson |
| 5,452,356 A | 9/1995 | Albert |
| 5,466,246 A | 11/1995 | Silvian |
| 5,481,255 A | 1/1996 | Albert et al. |
| 5,503,158 A | 4/1996 | Coppock et al. |
| 5,539,705 A | 7/1996 | Akerman et al. |
| 5,544,661 A | 8/1996 | Davis et al. |
| 5,735,285 A | 4/1998 | Albert et al. |
| 5,844,997 A | 12/1998 | Murphy, Jr. |
| 6,048,319 A | 4/2000 | Hudgins et al. |
| 6,264,614 B1 | 7/2001 | Albert et al. |
| 6,319,201 B1 | 11/2001 | Wilk |
| 6,377,843 B1 | 4/2002 | Naydenov et al. |
| 6,418,394 B1 | 7/2002 | Puolakanaho et al. |
| 6,549,756 B1 | 4/2003 | Engstrom |
| 6,685,633 B2 | 2/2004 | Albert et al. |
| 6,790,178 B1 | 9/2004 | Mault et al. |
| 6,820,057 B1 | 11/2004 | Loch et al. |
| 6,845,263 B2 | 1/2005 | Kawaguchi |
| 6,950,681 B2 | 9/2005 | Hofmann |
| 6,970,737 B1 | 11/2005 | Brodnick et al. |
| 7,018,339 B2 | 3/2006 | Birnbaum et al. |
| 7,031,745 B2 | 4/2006 | Shen |
| 7,107,095 B2 | 9/2006 | Manolas |
| 7,260,429 B2 | 8/2007 | Siejko et al. |
| 7,351,207 B2 | 4/2008 | Priemer |
| 7,383,297 B1 | 6/2008 | Atsmon et al. |
| 7,520,860 B2 | 4/2009 | Guion-Johnson et al. |
| 7,542,878 B2 | 6/2009 | Nanikashvili |
| 7,548,623 B2 | 6/2009 | Manabe |
| 7,603,148 B2 | 10/2009 | Michalak |
| 7,668,589 B2 | 2/2010 | Bauer |
| 7,742,808 B2 | 6/2010 | Nissilä |
| 7,819,814 B2 | 10/2010 | Gavriely et al. |
| 7,955,273 B2 | 6/2011 | Rahe-Meyer |
| 2001/0031998 A1 | 10/2001 | Nelson et al. |
| 2002/0111556 A1 | 8/2002 | Wegner |
| 2003/0004425 A1 | 1/2003 | Narimatsu et al. |
| 2003/0093002 A1 | 5/2003 | Kuo |
| 2004/0215088 A1 | 10/2004 | Hubelbank |
| 2004/0215094 A1 | 10/2004 | Baumer et al. |
| 2004/0220487 A1 | 11/2004 | Vyshedskiy et al. |
| 2004/0220488 A1 | 11/2004 | Vyshedskiy et al. |
| 2004/0266407 A1 | 12/2004 | Lee et al. |
| 2005/0014531 A1 | 1/2005 | Findikli |
| 2005/0078533 A1 | 4/2005 | Vyshedskiy et al. |
| 2006/0022833 A1 | 2/2006 | Ferguson et al. |
| 2006/0047215 A1 | 3/2006 | Newman et al. |
| 2006/0252999 A1 | 11/2006 | Devaul et al. |
| 2007/0021677 A1 | 1/2007 | Markel |
| 2007/0027386 A1 | 2/2007 | Such et al. |
| 2007/0063850 A1 | 3/2007 | Devaul et al. |
| 2007/0106179 A1 | 5/2007 | Bagha et al. |
| 2008/0146890 A1 | 6/2008 | LeBoeuf et al. |
| 2008/0171945 A1 | 7/2008 | Dotter |
| 2008/0214903 A1 | 9/2008 | Orbach |
| 2008/0293453 A1 | 11/2008 | Atlas et al. |
| 2009/0010461 A1 | 1/2009 | Klinghult et al. |
| 2009/0144080 A1 | 6/2009 | Gray et al. |
| 2009/0149767 A1 | 6/2009 | Rossetti |
| 2009/0156908 A1 | 6/2009 | Belalcazar et al. |
| 2009/0171170 A1 | 7/2009 | Li et al. |
| 2009/0209873 A1 | 8/2009 | Pinter et al. |
| 2009/0287067 A1 | 11/2009 | Dorogusker et al. |
| 2009/0312655 A1 | 12/2009 | Lo |
| 2010/0033303 A1 | 2/2010 | Dugan et al. |
| 2010/0035927 A1 | 2/2010 | Ojika et al. |
| 2010/0042008 A1 | 2/2010 | Amitai et al. |
| 2010/0049006 A1 | 2/2010 | Magar et al. |
| 2010/0094152 A1 | 4/2010 | Semmlow |
| 2010/0113950 A1 | 5/2010 | Lin et al. |
| 2010/0148956 A1 | 6/2010 | Song et al. |
| 2010/0217099 A1 | 8/2010 | LeBoeuf et al. |
| 2010/0217100 A1 | 8/2010 | LeBoeuf et al. |
| 2010/0217345 A1 | 8/2010 | Wolfe et al. |
| 2010/0256509 A1 | 10/2010 | Kuo et al. |
| 2011/0015496 A1 | 1/2011 | Sherman et al. |
| 2011/0035927 A1 | 2/2011 | Griffin et al. |
| 2011/0301439 A1 | 12/2011 | Albert et al. |
| 2012/0172689 A1 | 7/2012 | Albert et al. |

FOREIGN PATENT DOCUMENTS

| | | |
|---|---|---|
| JP | 2002191562 A | 7/2002 |
| WO | WO 88/05282 A1 | 7/1988 |
| WO | 90/08361 | 7/1990 |
| WO | 92/06551 | 4/1992 |
| WO | WO 98/38611 A1 | 9/1998 |
| WO | WO 00/41620 A1 | 7/2000 |
| WO | WO 2004/037080 A1 | 5/2004 |
| WO | WO 2007/014545 A2 | 2/2007 |
| WO | WO2010/113354 | 10/2010 |
| WO | WO 2010/144626 A1 | 12/2010 |
| WO | WO 2011/006356 A1 | 1/2011 |
| WO | WO 2011/008838 A1 | 1/2011 |
| WO | WO 2011/014292 A1 | 2/2011 |
| WO | WO 2011/022942 A1 | 3/2011 |
| WO | WO 2011/040877 A1 | 4/2011 |

OTHER PUBLICATIONS

"Choice Portable Handheld ECG EKG Monitor"; printed from website http://www.amazon.com/Choice-Portable-Handheld-ECG-Monitor/dp/B001Q74VOM; printed on Mar. 26, 2010; 1 page.

"Omron Portable ECG Monitor"; printed from website http://www.target.com/gp/detail.html; printed on Mar. 26, 2010; 1 page.

"Handheld ECG Monitor—Handheld EKG Monitor at Favoriteplus.com"; printed from website www.favoriteplus.com/handheld-ecg-ekg-monitor; printed on Feb. 4, 2010; 3 pages.

"Handheld Easy ECG Monitor—Handheld Easy EKG Monitor"; printed from website www.favoriteplus.com/easy-ecg-handgeld-monitor-fp; printed on Feb. 4, 2010; 2 pages.

"PC-80B Portable ECG Monitor w/sd card extension slot"; printed from website www.amazon.com/Portable-Monitor-extension-leather-shipping/dp/B001OjWKUE; printed on Feb. 4, 2010; 5 pages.

"New Professional Quality ECGEKG Portable Heart Monitor"; printed from website http://cgibay.com/ws/eBayISAPI.dll; printed on Feb. 4, 2010; 3 pages.

"Handheld ECG Monitor—Handheld EKG Monitor InstantCheck"; printed from website http://www.favoriteplus.com/instanchcheck-handheld-ecg-ekg-monitor; printed on Feb. 4, 2010; 2 pages.

"ECG Machine Handheld ReadMyHeart"; printed from website http://www.helioliving.com/ECG-Machine-Handheld-ReadMyHeart; printed on Feb. 4, 2010; 1 page.

"Omron Portable ECG EKG Handheld HCG-801 Monitor"; printed from website http://www.amazon.com/Omron-Portable-Handheld-HCG-801-Monitor/dp/B0019WH3EO; printed on Feb. 24, 2010; 5 pages.

"Handheld ECG Monitor MD100A1"; printed from website http://www.choicemmed.com/productshow.asp; printed on Dec. 28, 2009; 2 pages.

"Card Guard CG-6108 ACT Ambulatory Cardiac Telemetry Brochure"; Card Guard; The Telemedicine Company; Switzerland; 2006; 2 pages.

"IMEC News; IMEC extends flexible ECG patch to enable arrhythmia detection"; printed from website http://www2.imec.be/imec; printed on Aug. 18, 2009 1 page.

"GEMS AIR"; printed from website http://www.cardiocommsolutions/com; printed on Mar. 19, 2010; 1 page.

"Handheld ECG Monitor MD100B"; printed from website http://www.choicemmed.com/productshow.asp; printed on Dec. 28, 2009; 2 pages.

"Adidas miCoach Pacer Review: Like Nike+, Only Better"; printed from website http://gizmodo.com/5479456/adidas; printed on Mar. 4, 2010; 5 pages.

"The Arrhythmia Monitoring System; King of Hearts Express AF Recorder" Brochure from Instromedix; A CardGuard Company; Rosemont, IL; 2004; 3 pages.

Woodward et al; "Bio-Potential-To-Frequency Converter/Modulator"; Electronic Design; Aug. 1999; p. 117.

"Heartplus Micro"; printed from website http://www.designawards.com/au; printed pn Apr. 12, 2002; 6 pages.

Grier, James W.; "How to use 1-lead ECG recorders to obtain 12-lead resting ECGs and exercise ("stress") ECGs"; Department of Biological Sciences: printed from website http://www.ndsu.edu/pubweb/~grier; printed on Jun. 7, 2010; 13 pages.

"Transtelephonic Cardiac Event Recording for Arrhythmia Surveillance"; printed from website http://tchin.org/resource_room/c_art; printed on Mar. 26, 2010; 2 pages.

"Square payment dongle demoed for iPhone toting hippies and you (video)"; printed from website http://www.engadget.com/2010/01/18/square-payment; printed on Jan. 18, 2010; 6 pages.

"RedEye mini converts iPhone, iPad or iPod touch into IR-beaming universal remote"; printed from website http://www.engadget.com/2010/03/02/redeye; printed on Mar. 2, 2010; 3 pages.

"Power A's New Case Turns Your iPhone Into a Universal Remote"; printed from website http://appadvice.com/appnn; printed on Mar. 1, 2010; 2 pages.

"EPI Life phone sports ECG function, can let doctors know if you're not gonna make it"; printed from website http://www.engadget.com/2010/06/16/epi-life-phone-sports: printed on Jun. 17, 2010; 4 pages.

"M/CardioMobile: Remote Wireless Cardiac Rehabilitation Monitoring" printed from website http://alivetec.cable.nu/cardiomobile; 1 page.

Cheng, Allen C.; "Real-Time Cardiovascular Diseases Detection on a Smartphone" Departments of Electrical and Computer Engineering, Bioengineering, Neurological Surgery and Computer Science; University of Pittsburgh, Pittsburgh, PA.

Muench, Frederick PhD; "HRV: The Manufacturers and Vendors Speak; The portable StressEraser Heart Rate Variability Biofeedback Device: Background and Research"; Biofeedback vol. 36, Issue 1, pp. 35-39.

"The Author's Metrics"; Wired Magazine Article; New York, NY; Jul. 2009; p. 93-126.

"Cardiac Event Recording FAQs"; Instromedix A Card Guard Company, San Diego, CA.

"Mauvila ECG Tutorial"; Basic ECG Interpretation Tutorial; Sections 1-12; printed from website http://mauvila.com/ECG/ecg.htm; printed on Mar. 26, 2010; 56 pages.

"Handheld ECG Monitor" Brochure; M Med Choice, Beijing Choice Electronic Technology Co., LTD.;6 pages.

"The Networked Body" Magazine Article from FAST TALK Magazine; Jul./Aug. 2009; pp. 19-26.

"Med Choice" printed from website http://www.choicemmed.con/1xwm.asp; printed on Dec. 28, 2009; 1 page.

Kumparak, Greg; "Visa officially announces their case that turns your iPhone into a credit card (and we've got pics!)"; May 17, 2010; printed from website www.mobilecrunch.com; printed on Feb. 3, 2011.

Ziegler, Chris; "EPI Life phone sports ECG function, can let doctors know if you're gonna make it"; printed from website www.engadget.com/2010/06/; Jun. 17, 2010.

Hannaford, Kat; "How to Turn Your iPhone Into a Laser, Fan or Flashlight"; printed from website http://m.gizmodo.com/5534904; printed on Feb. 3, 2011.

Stevens, Tim; "Apple's Seamlessly Embedded Heart Rate Monitor could turn the iPhone into a new-age mood ring"; May 6$^{th}$, 2010; printed from website www.engageget.com; printed on Feb. 3, 2011.

Vanhemert, Kyle; "XWave Headset Lets You Control iPhone Apps With Your Brain"; Sep. 8, 2010; printed from website http://gizmodo.com; printed on Sep. 8, 2010.

"M/CardioMobile: Remote Wireless Cardiac Rehabilitation Monitoring" printed from website http://alivetec.cable.nu/cardiomobile; printed on or before Apr. 14, 2010.

Cheng, Allen C.; "Real-Time Cardiovascular Diseases Detection on a Smartphone"; Departments of Electrical and Computer Engineering, Bioengineering, Neurological Surgery and Computer Science; University of Pittsburgh; Pittsburgh, PA; printed on or before Apr. 14, 2010.

Muench, Frederick, PhD; "HRV: The Manurfacturers and Vendors Speak; The portable StressEraser Heart Rate Variability Biofeedback Device: Background and Research"; Biofeedback vol. 36, Issue 1, pp. 35-39; published Spring 2008.

"Cardiac Event Recording FAQ's"; Instromedix A Card Guard Company, San Diego, CA.; printed from website www.instromedix.com/pdf/products/cardiac; printed on or before Apr. 14, 2010.

"Handheld ECG Monitor" Brochure; M Med Choice, Beijing Choice Electronic Technology Co., LTD.; published on or before Apr. 14, 2010.

Prystowsky, M.D.; "Chairmans Introduction"; Duke University Medical Center; Indianapolis, Indiana; (no date); pp. 5-6; printed on or before Apr. 14, 2010.

Hayes, M.D.; "Approaches to Diagnosing Transient Arhythmias" An Overview; Mayo Clinic; Rochester Minnesota; (no date); pp. 7-10; printed on or before Apr. 14, 2010.

Ferrick, M.D.; "Holter Monitoring and cardiac Event Recording in Assessing Symptomatic Patients"; Albert Einstein College of Medicine; Bronx, New York; (no date); pp. 11-14; printed on or before Apr. 14, 2010.

Bajaj, M.D.; "Event Recording in Ambulatory Patients with Syncopal Events"; University of Kansas; Wichita, Kansas; (no date); pp. 15-18; printed on or before Apr. 14, 2010.

Prystowsky, M.D. "The Clinical Application, Diagnositc Yield and Cost considerations of Cardiac Event Recorders"; Duke University Medical Center; Indianapolis, Indiana; (no date); pp. 19-23; printed on or before Apr. 14, 2010.

Gillette, M.D.; "Diagnosis of Pediatric Arrhythmias with Event Recording"; Medical University of South Carolina; Charleston, South Carolina; (no date); pp. 25-32; printed on or before Apr. 14, 2010.

Semler, M.D.; "The Future of Cardiac Event Monitoring"; St. Vincent Hospital and Medical Center; Portland Oregon; (no date); pp. 33-37; printed on or before Apr. 14, 2010.

Prystowsky, M.D.; "Chairmans Summary"; Duke University Medical Center; Indianapolis, Indiana; (no date); pp. 39-40; printed on or before Apr. 14, 2010.

"Observer Hand-held ECG Monitor MD100B"; (no date); printed on or before Apr. 14, 2010.

Vanhemert, Kyle; "XWave Headset Lets You Control iPhone Apps With your Brain"; Jul. 9, 2010; printed from website http://gizmodo.com; printed on Jul. 9, 2010.

Elert, Glenn (Editor); Frequency Range of Human Hearing; The Physics Factbook; web version as of Mar. 29, 2010; 2 pgs.; printed Jun. 6, 2012 (http://web.archive.org/web/20100329141847/http://hypertextbook.com/facts/2003/ChrisDAmbrose.shtml).

Hearing Loss Assoc. of Kentuckiana; Decibal Ratings/Hazardous Time Exposures of Common Noise (excerpt from Survivor's Manual); web version as of Oct. 5, 2008; 2 pgs.; printed Jun. 6, 2012 (http://web.archive.org/web/20081005143856/http://www.hearinglossky.org/hlasurvival1.html).

Huang, Tina; Age-related hearing loss; Minnesota Medicine; 90(10); pp. 48-50; Oct. 2007; printed Jun. 6, 2012 from: http://www.minnesotamedicine.com/PastIssues/PastIssues2007/October2007/ClincalHuangOctober2007.aspx).

Neuroreille; Audiometry; web version as of Oct. 14, 2008; 1 pg.; printed Jun. 6, 2012 (http://www.neuroreille.com/promenade/english/audiometry/audiometry.htm).

Perez, Sarah; No NFC? No Problem; New Startup Zoosh Provides Workaround Technology (Jun. 20, 2011); printed on or before Jun. 27, 2011 from website; 2 pgs.; (http://www.readwriteweb.com/archives).

Wikimedia Laboratories; Acoustics; web archive version dated Jan. 25, 2009; 2 pgs.; printed Jun. 6, 2012 (http://liveweb.archive.org/http://en.labs.wikimedia.org/wiki/Acoustics).

Wikipedia; Aliasing; web version as of Apr. 3, 2011; 5 pgs.; printed Jun. 6, 2012 (http://liveweb.archive.org/http://en.wikipedia.org/w/index.php?title=Aliasing&oldid=422141882).

Wikipedia; Hearing Range; web version as of Feb. 6, 2010; 5 pgs.; printed Jun. 6, 2012 (http://web.archive.org/web/20100206213741/http://en.wikipedia.org/wiki/Hearing_range).

Albert et al.; U.S. Appl. No. 13/752,048 entitled "Ultrasonic digital communication of biological parameters," filed Jan. 28, 2013.

Vitaphone 2300; www.free2move.us/News/NewsVitaphone_240105.htm; printed May 12, 2010.

Information for Medical Applications, Texas Instruments, "Biophysical Monitoring—Electrocardiogram (ECG) Front End", 2004, 2 pages.

"Pulse oximetry", printed from website http://en.wikipedia.org on May 10, 2010, 4 pages.

Stevens, "Apple's Seamlessly Embedded Heart Rate Monitor could turn the iPhone into a new-age mood ring", printed from the website http://www.engadget.com on May 6, 2010, 3 pages.

Fulford-Jones, et al., "A Portable, Low-Power, Wireless Two-Lead EKG System", Division of Engineering and Applied Sciences, Harvard University, Sep. 2004, 4 pages.

Dobrev, et al., Bootstrapped two-electrode biosignal amplifier, Med Biol Eng Comput, 2008, 7 pages.

Deveau, "Health Care eyes smart phones to heal ills", printed from the website http://www.theglobeandmail.com on Sep. 17, 2009, 4 pages.

Kim, et al., "Detection of Atrial Fibrillation Episodes using Multiple Heart Rate Variability Features in Different Time Periods", 2008, 4 pages.

Puurtinen, et al., Best Electrode Locations for a Small Bipolar ECG Device: Signal Strength Analysis of Clinical Data, Annals of Biomedical Engineering, vol. 37, No. s 2, Feb. 2009 (© 2008) pp. 331-336.

Salahuddin, et al., "Ultra Short Term Analysis of Heart Rate Variability using Normal Sinus Rhythm and Atrial Fibrillation ECG Data", Engineering in Medicine and Biology Society, Aug. 2007, pp. 4656-4659.

Leijdekkers et al., "Trial Results of a Novel Cardiac Rhythm Management System using Smart Phones and wireless ECG Sensors", Proceedings of the 7th International Conf. On Smart homes and health Telematics., Jul. 1-3, 2009, Tours, France.

Oresko, et al., "Detecting Cardiovascular Diseases via Real-Time Electrocardiogram Processing on a Smartphone", 2009 Workshop on Biomedicine in Computing: Systems, Architectures, and Circuits, pp. 13-16.

Raju Heart-Rate and EKG Monitor Using the MSP430FG439, SLAA280—Oct. 2005-Revised Sep. 2007, 11 pages.

Prystowsky , M.D., "Chairmans Introduction", Indianapolis, Indiana (no date), pp. 5-6.

Hayes, M.D., Approaches to Diagnosing Transient Arrhythmias—An Overview, Rochester Minnesota (no date) pp. 7-10.

Ferrick, M.D., Holter Monitoring and Cardiac Event Recording in Assessing Symptomatic Patients, Bronx, New York, (no date) pp. 11-14.

Bajaj, M.D., Event Recording in Ambulatory Patients with Syncopal Events, Wichita, Kansas, (no date) pp. 15-18.

Prystowsky, M.D., "The Clinical Application, Diagnostic Yield and Cost Considerations of Cardiac Event Recorders", Indianapolis, Indiana (no date) pp. 19-23.

Gillette, M.D., "Diagnosis of Pediatric Arrhythmias with Event Recording", Charleston, South Carolina (no date) pp. 25-32.

Semler, M.D., "The Future of Cardiac Event Monitoring", Portland, Oregon (no date) pp. 33-37.

Prystowsky, M.D., "Chairmans Summary" (no date) pp. 39-40.

Bramanti et al., Multichannel telemetric system for biomedical signals via switched telephone lines, Medical and Biological Engineering and Computing, Sep. 1982, vol. 20, No. 5, pp. 653-656.

Hartmann, "ECG Front-End Design is Simplified with MicroConverter" Analog Dialogue, Nov. 2003, vol. 37, pp. 1-5.

Burke, "A Micropower Dry-Electrode ECG Preamplifier", IEEE Transactions on Biomedical Engineering, Feb. 2000, vol. 47, No. 2, pp. 155-162.

Levkov et al., "Removal of power-line interference from the ECG: a review of the subtraction procedure" BioMedical Engineering OnLine 2005, printed from website http://www.biomedical-engineering-online.com/content/4/1/50, pp. 1-18.

"Headset Profile (HSP)", printed from website http://bluetooth.com/English/Techmologv/Works/Pates/HSP.aspx, printed on May 12, 2010.

"Zio Patch Wins Medical Design Award" MedGadget internet journal of emerging medical technologies, printed from website http://medgadget.com/archives/2010/04/zio_patch_wins_medial_design_award_1.html.

Kumar, M.D., "Zio Patch", printed from website http://www.irhvthmtech.com/zio-solution/zio-pach/, printed on Apr. 12, 2010.

"Use your Treo 650 as a portable ECG monitoring device", Mobility Mind Celebrating mobile Internet lifestyle and culture, Sep. 14, 2005, printed from website http://www.treotoday.net/2005/09/14/use-your-treo-650-as-a-portable-ecg-monitoring-device/.

"Smartphone may keep the cardiologist away", The Independent, Health & Families, Mar. 5, 2010, printed from website http://www.independent.co.uk/life-style/health-and-families/health-news/smartphone-may-keep-the-cardiologist-away-1916652.html, printed on Mar. 26, 2010.

"Wireless ECG Monitoring System", printed from website http://www.alibaba.com/product-gs/248168581/Wireless_ECG_Monitoring_system.html., printed on Mar. 26, 2010.

"Observer Hand-held ECG Monitor MD100B" printed on or before Apr. 14, 2010.

* cited by examiner

HEART MONITORING SYSTEM USABLE WITH A SMARTPHONE OR COMPUTER

CROSS REFERENCE TO RELATED APPLICATIONS

Not Applicable.

STATEMENT REGARDING FEDERALLY SPONSORED RESEARCH OR DEVELOPMENT

Not applicable.

BACKGROUND

1. Field of Invention

The presently claimed and disclosed inventive concept(s) relates generally to personal physiology monitoring devices and methods and, more particularly, but not by way of limitation, to devices, systems and software for providing ECG, heart rate and cardiac arrhythmia monitoring utilizing a computing device such as a smartphone.

2. Background of the Invention

The prior art includes numerous systems wherein ECG data or the like is monitored and/or transmitted from a patient to a particular doctor's office or health service center. For example, U.S. Pat. No. 5,735,285 discloses use of a handheld device that converts a patient's ECG signal into a frequency modulated audio signal that may then be analyzed by audio inputting via a telephone system to a selected handheld computer device or to a designated doctor's office. Similarly, U.S. Pat. No. 6,264,614 discloses a heart monitor, which is manipulated by the patient to sense a biological function such as a heart beat, and outputs an audible signal to a computer microphone. The computer processes the audible signal and sends resulting data signals over a network or Internet. U.S. Pat. No. 6,685,633 discloses a heart monitor that a patient can hold against his or her chest. The device outputs an audible signal responsive to the function or condition, such as the beating of the heart, to a microphone connected to a computer.

U.S. Pat. App. Publication No. 20100113950 discloses an electronic device having a heart sensor including several leads for detecting a user's cardiac signals. The leads are coupled to interior surfaces of the electronic device housing to hide the sensor from view. Using the detected signals, the electronic device can then identify or authenticate the user.

Limitations of the prior art utilizing acoustic signals include a signal to noise ratio that is diminished by talking or any other noisy activity in the vicinity, thus potentially jeopardizing the integrity of the heart monitoring data signals. Additionally, the audible signals can be heard by anyone in the vicinity of the computer and heart monitor, which can be bothersome to the user as well as to others in the vicinity. Other applications fail to provide a reliable, inexpensive personal monitoring device that is readily compatible with existing computing devices such as smartphones. It would be advantageous if these issues were addressed in a personal monitoring device transmitting real time physiological data.

SUMMARY OF THE INVENTION

Embodiments of the presently claimed and disclosed invention are directed to a personal monitoring device having a sensor assembly configured to sense physiological signals upon contact with a user's skin. The sensor assembly produces electrical signals representing the sensed physiological signals. A converter assembly, integrated with, and electrically connected to the sensor assembly, converts the electrical signals generated by the sensor assembly to a frequency modulated physiological audio signal. In one embodiment, the frequency modulated physiological audio signal has a carrier frequency in the range of from about 6 kHz to about 20 kHz.

In another embodiment, the personal monitoring device includes a cable connected to the converter assembly for transmitting the frequency modulated physiological audio signal to a 3.5 mm headphone jack on a smartphone, wherein the converter assembly is electrically isolated from the smartphone by an audio isolation transformer. In this case, the frequency modulated physiological audio signal has a carrier frequency in the range of from about 1 kHz to about 20 kHz.

In yet another embodiment, the personal monitoring device includes a wireless radio transmitter configured to utilize Bluetooth® headset technology to transmit the frequency modulated physiological audio signal, having a carrier frequency in the range of from about 1 kHz to about 20 kHz, to a Bluetooth® enabled computing device.

An ECG device of the presently claimed and disclosed inventive concept(s) includes an electrode assembly configured to sense heart-related signals upon contact with a user's skin, and to convert the sensed heart-related signals to an ECG electric signal. A converter assembly, integrated with, and electrically connected to the electrode assembly, is configured to convert the electric ECG signal generated by electrode assembly to a frequency modulated ECG audio signal having a carrier frequency in the range of from about 6 kHz to about 20 kHz.

In one embodiment, a smartphone protective case, usable as an ECG device, is provided. An electrode assembly, configured to sense heart-related signals upon contact with a user's skin, and to convert the sensed heart-related signals to an ECG electric signal, is provided. A converter assembly, integrated with, and electrically connected to the electrode assembly, is configured to convert the electric ECG signal generated by the electrode assembly to a frequency modulated ECG audio signal having a carrier frequency in the range of from about 6 kHz to about 20 kHz, and further configured to output the ECG audio signal through an audio transmitter at a signal strength capable of being received by a smartphone positioned within the smartphone protective case.

In a second embodiment, an ECG device is provided in a housing having an electrode assembly configured to sense heart-related signals upon contact with a user's skin, and to convert the sensed heart-related signals to an ECG electric signal. A converter assembly integrated with, and electrically connected to the electrode assembly, is configured to convert the electric ECG signal generated by electrode assembly to a frequency modulated ECG audio signal having a carrier frequency in the range of from about 6 kHz to about 20 kHz, and further configured to output the ECG audio signal through an audio transmitter at a signal strength capable of being received by a smartphone located near the ECG device.

In another embodiment, an ECG device is provided having an electrode assembly configured to sense heart-related signals upon contact with a user's skin, and to convert the sensed heart-related signals to an ECG electric signal. A converter assembly integrated with, and electrically connected to the electrode assembly, is configured to convert the electric ECG signal generated by electrode assembly to a frequency modulated ECG audio signal. A cable is provided for transmitting the frequency modulated ECG audio signal to a 3.5 mm headphone jack on a smartphone, wherein the converter assembly is electrically isolated from the smartphone by an audio isolation transformer.

In yet another embodiment, a computer-readable storage medium is provided for storing a set of instructions capable of being executed by one or more computing devices, causing the one or more computing devices to digitize and demodulate a frequency modulated ECG audio signal having a carrier frequency in the range of from about 6 kHz to about 20 kHz to produce real time demodulated digital ECG data, and to display on a display screen of the computing device, the real time ECG signal represented by the demodulated digital ECG data.

Thus, utilizing (1) the technology known in the art; (2) the above-referenced general description of the presently claimed and disclosed inventive concept(s); and (3) the detailed description of the invention that follows, the advantages and novelties of the presently claimed and disclosed inventive concept(s) would be readily apparent to one of ordinary skill in the art.

DETAILED DESCRIPTION OF THE INVENTION

Before explaining at least one embodiment of the invention in detail, it is to be understood that the invention is not limited in its application to the details of construction, experiments, exemplary data, and/or the arrangement of the components set forth in the following description. The invention is capable of other embodiments or of being practiced or carried out in various ways. Also, it is to be understood that the terminology employed herein is for purpose of description and should not be regarded as limiting.

Figure 1:
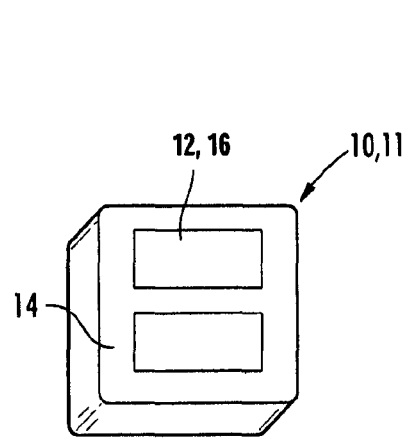
FIG. 1 is a schematic representation of an embodiment of a personal monitoring device of the present invention.
Figure 2:
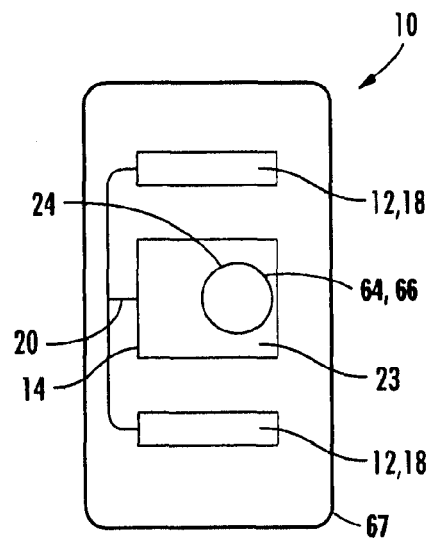
FIG. 2 is a schematic representation of another embodiment of a personal monitoring device of the present invention.

The presently claimed and disclosed inventive concepts provide a personal monitoring device 10, embodiments of which are shown schematically in FIGS. 1 and 2. The acquisition electronics 11 of the monitoring device 10 includes a sensor assembly 12 configured to sense physiological signals upon contact with a user's skin. The sensor assembly 12 produces electrical signals representing the sensed physiological signals, which input to a converter assembly 14, integrated with the sensor assembly 12. Converter assembly 14 converts the electrical signals generated by the sensor assembly 12 to a frequency modulated physiological audio signal having a carrier frequency in the range of from about 1 kHz to about 20 kHz. In one embodiment, the frequency modulated physiological audio signal has a carrier frequency in the range of from about 6 kHz to about 20 kHz.

The sensor assembly 12 can include any suitable sensor operative to detect a physiological signal that a user desires to monitor. Nonlimiting examples of such physiological signals include, but are not limited to, respiration, heart beat, heart rate, electrocardiogram (ECG), electromyogram (EMG), electrooculogram (EOG), pulse oximetry, photoplethysmogram (PPG) and electroencephalogram (EEG).

Figure 3:
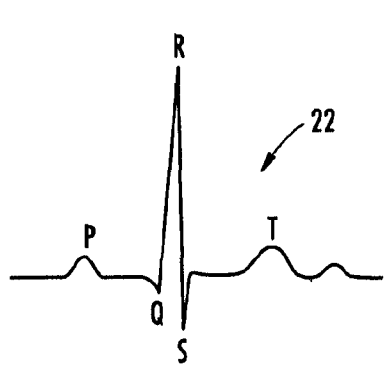
FIG. 3 is an example of graphical ECG representation.

A respiration detector can be a conventional microphone assisted stethoscope 16. Heart beat and heart rate can be detected as well using a conventional microphone assisted stethoscope 16, or by using an electrode assembly 18 to sense electrical signals generated by the heart over time. Such electrodes 18 can also be used to detect the electrical activity of the heart over time for electrocardiography (ECG). An ECG is a measurement of the small electrical changes on the skin generated when the heart muscle depolarizes during each heart beat. The output from a pair of electrodes 18 is known as a lead 20. Small rises and falls in the voltage between two electrodes placed on either side of the heart can be processed to produce a graphical ECG representation 22 such as the example ECG shown in FIG. 3.

Electromyography (EMG) detects the electrical potential generated by muscle cells when the cells are electrically or neurologically activated. The signals can be analyzed to detect medical abnormalities. Electrooculography (EOG) is a technique for measuring the resting potential of the retina. Usually, pairs of electrodes 18 are placed either above and below the eye, or to the left and right of the eye, and a potential difference measurement is a measure for the eye position.

The oxygenation of a person's hemoglobin can be monitored indirectly in a noninvasive manner using a pulse oximetry sensor, rather than measuring directly from a blood sample. The sensor is placed on a thin part of the person's body, such as a fingertip or earlobe, and a light containing both red and infrared wavelengths is passed from one side to the other. The change in absorbance of each of the two wavelengths is measured and the difference used to estimate oxygen saturation of a person's blood and changes in blood volume in the skin. A photoplethysmogram (PPG) can then be obtained using the pulse oximeter sensor or with an optical sensor using a single light source. The PPG can be used to measure blood flow and heart rate. An electroencephelogram (EEG) can be monitored using electrodes attached to the scalp and measures voltages generated by brain activity.

The converter assembly 14 converts the electrical signals generated by the sensor assembly 12 to a frequency modulated physiological audio signal that can be received by a computing device 13. In the embodiment shown in FIG. 2, the converter assembly 14 includes a converter 23 and an audio transmitter 24 for outputting frequency modulated physiological signals having a carrier frequency in the range of from about 6 kHz to about 20 kHz as frequency modulated acoustic signals. Nonlimiting examples of suitable audio transmitters 24 include, but are not limited to, miniature speakers, piezoelectric buzzers, and the like. The acoustic signals can be received by, for example, a microphone 25 in a computing device 13 such as a smartphone, personal digital assistant (PDA), tablet personal computer, pocket personal computer, notebook computer, desktop computer, server computer, and the like.

Prior art devices have used frequency modulated physiological signals to communicate between acquisition hardware and a computing device. The signals have a carrier frequency within the audible range such as the traditional 1.9 kHz FM frequency used to transmit ECG signals. However, it has been discovered that by using "high frequency" audio frequencies as the carrier, such as frequencies in the range of from about 6 kHz to about 20 kHz, the acoustic communication between the acquisition electronics 11 of the personal monitoring device 10, and a computing device 13 such as a smartphone, is virtually silent and far more noise-immune than the traditional 1.9 kHz FM ECG frequency. In fact, measurements of the audio signal power in the 1.5 kHz to 15 kHz range determined that carrier frequencies of 6 kHz and higher provide communication that is immune to ambient and voice "noise" contamination. Also, by using a carrier frequency in the 10 kHz to 15 kHz range, we create both a lower noise and a silent communication between the acquisition electronics 11 and the computing device 13 or smartphone. An additional reason for using high carrier frequencies, such as in the 6 kHz to 15 kHz range or in the 10 kHz to 15 kHz range, is to allow simultaneous recording of voice and physiological signals over a single audio channel, where voice and the FM signal are in different frequency bands that can be filtered and separated. The clinical applications of this embodiment can include fast and inexpensive cardiac rhythm diagnosis for physicians as well as personal ECG acquisition for patients.

Figure 4:
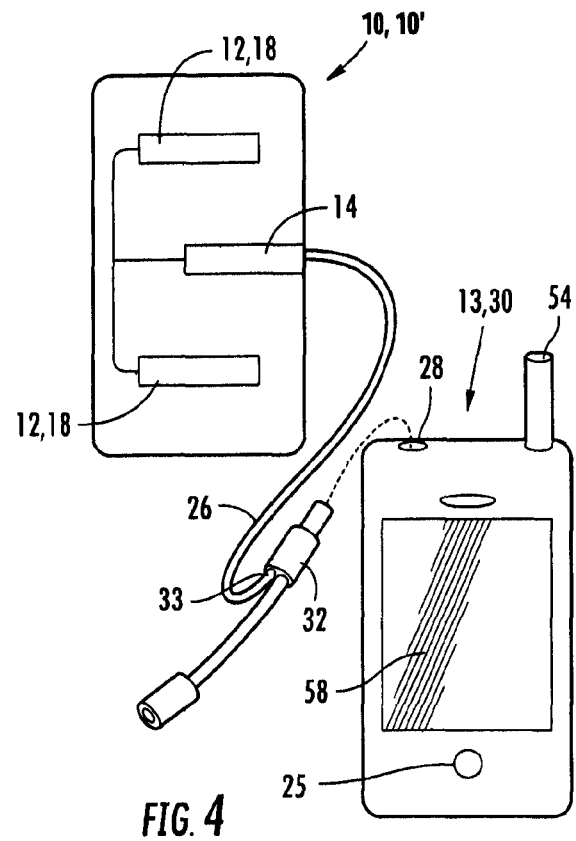
FIG. 4 is a schematic representation of an embodiment wherein a personal monitoring device includes an audio cable that can input to a smartphone.

In another embodiment, such as that shown in FIG. 4, the converter assembly 14 is configured to convert the electrical signals generated by the sensor assembly 12 to a frequency modulated physiological audio signal which is transmitted by a cable 26 to a 3.5 mm headphone jack 28 on a smartphone 30. This configuration is totally silent and immune to ambient acoustic noise. In this embodiment the converter assembly 14 is electrically isolated from the smartphone 30 by an audio isolation transformer 32. The audio isolation transformer 32 preferably conforms to medical safety performance standards such as, for example, those outlined in IEC 60601 along with national and regional deviations. The cable 26 for transmitting the frequency modulated ECG audio signal to the 3.5 mm headphone jack 28 on the smartphone 30 can include a splitter 33 configured, as understood by those skilled in the art, to allow the user to listen to music and voice messages while transmitting the frequency modulated ECG audio signal. The splitter 33 can also allow the user to utilize a mic or headset to record spoken voice messages, such as comments and notes regarding physical symptoms, simultaneously with the ECG audio signal. Using a high carrier frequency of around 10 kHz, or in the 6 kHz to 20 kHz range, allows simultaneous recording of voice and physiological signals over a single audio channel, where the voice and the frequency modulated signal are in different frequency bands that can be readily filtered and separated.

Figure 5:
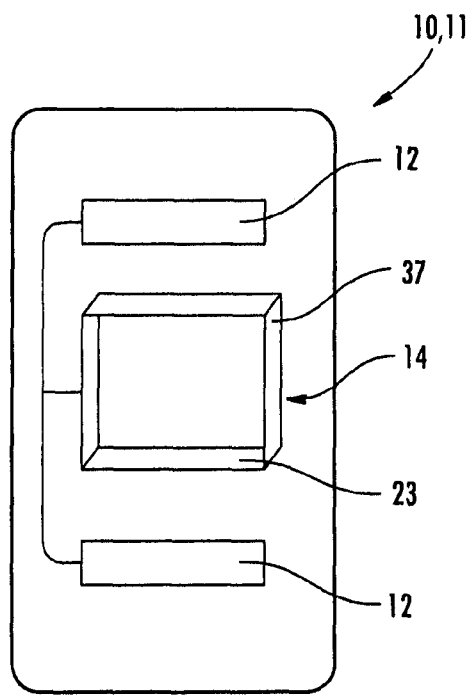
FIG. 5 is a schematic representation of an embodiment of an ECG device of the present invention utilizing a wireless radio transmitter.
Figure 6:
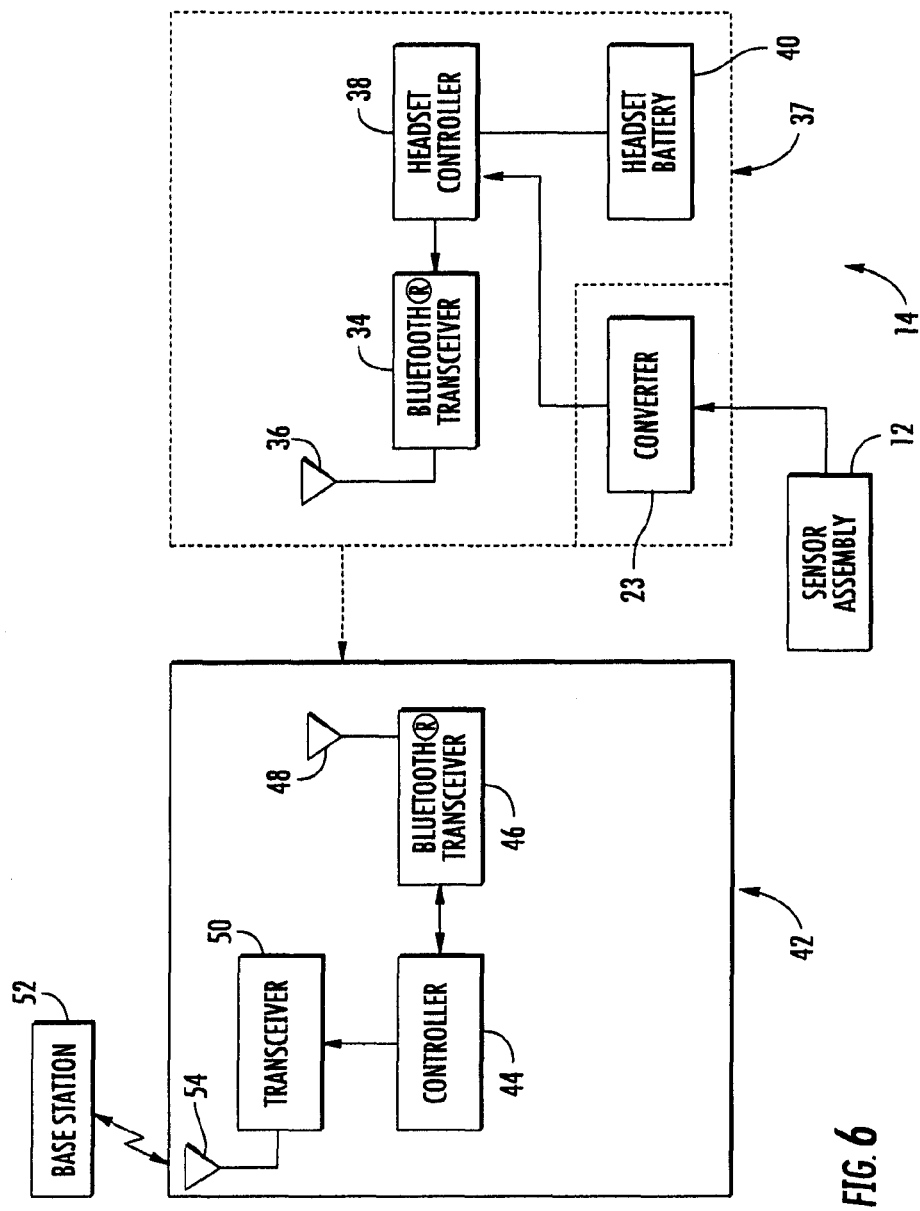
FIG. 6 is a schematic representation of an embodiment of a personal monitoring device of the present invention connecting via Bluetooth® to a computing device.

In yet another embodiment, shown in FIGS. 5 and 6, the converter assembly 14 includes a wireless radio transmitter 37 configured to convert and transmit the electrical signals generated by the sensor assembly 12 using a headset profile (HSP) of the Bluetooth® wireless communications standard is defined by the Bluetooth Special Interest Group (SIG) and available at URL address www.bluetooth.org. The electrical signals generated by the sensor assembly 12 are converted and transmitted using a Bluetooth® transceiver 34 and antenna 36 and communicated to the computing device 13, preferably a smartphone 30, according to instructions provided by a headset controller 38. Economy, as well as isolation and convenience, are provided by using a commercially available headset controller 38, Bluetooth® transceiver 34, and antenna 36, powered by a headset battery 40, wherein the electronics are commercially configured and mass-produced for communicating with computing devices 13 such as smartphones 30.

Computing device electronics 42 typically include a controller 44, a Bluetooth® transceiver 46 and antenna 48 for receiving input from a wireless Bluetooth® device. Most computing devices, and all smartphones, include a memory 56, a display screen 58, and a transceiver 50 for transmitting/receiving information signals to/from a base station or web server 52 via a cellular antenna 54. Thus, the computing device electronics 42 can be used to store information from the personal monitoring device 10 in memory 56, and/or transmit the information to the base station 52 or a specific communication address via wireless communication technology well understood by those skilled in the art.

In some cases, the personal monitoring device 10 can be considered an ECG device 10' and includes an electrode assembly 18 configured to sense heart-related signals upon contact with a user's skin, and to convert the sensed heart-related signals to an ECG electric signal. As discussed in detail hereinafter, the ECG device 10' transmits a frequency modulated ECG audio signal to a smartphone 30 via a wired audio jack connection, a wireless headset, or acoustically. Software running on the smartphone 30 digitizes and processes the audio in real-time, where the frequency modulated ECG signal is demodulated. The ECG can be further processed using algorithms to calculate heart rate and identify arrhythmias. The ECG, heart rate, and rhythm information can be displayed on the smartphone 30, stored locally for later retrieval, and/or transmitted in real-time to a web server 52 via a 2G/3G, WiFi or other Internet connection on the smartphone 30. In addition to the display and local processing of the ECG data, the smartphone 30 can transmit, in real-time, the ECG, heart rate and rhythm data via a secure web connection for viewing, storage and further analysis via a web browser interface (using the 2G/3G or WiFi connectivity of the smartphone 30). Server software provides for storage, further processing, real-time or retrospective display and formulation of a PDF ECG rhythm strip document and/or other reports and formats for printing remotely or locally.

In one embodiment, the converter assembly 14 of ECG device 10' is integrated with, and electrically connected to the electrode assembly 18 and is configured to convert the electric ECG signal generated by electrode assembly 18 to a frequency modulated ECG audio signal having a carrier frequency in the range of from about 6 kHz to about 20 kHz. It is sometimes desirable to utilize a carrier frequency in the 10 kHz to 15 kHz range in order to create both a lower noise and a silent communication between the acquisition electronics 11 and the computing device 13 or smartphone 30.

Figure 7:
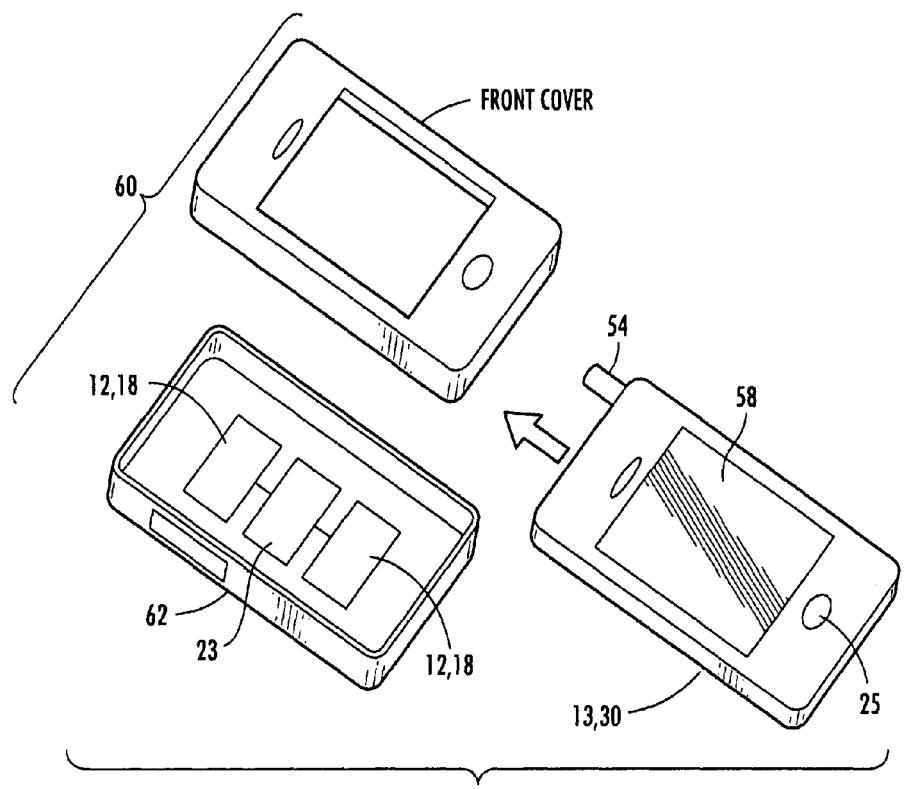
FIG. 7 is a schematic representation of an embodiment of a personal monitoring device of the present invention.

In one configuration, the ECG device 10' is usable as a smartphone protective case 60 as shown in FIG. 7. One example configuration utilizes a "slip-on" protective case 60 for an iPhone® or other smartphone 30, the protective case 60 including an integrated ECG electrode assembly 18 and acquisition electronics 11 (2, 3 or 4 electrodes for generating a single lead of ECG data). The ECG electrodes are located on the side 62 of the case 60 opposite of the display screen 58. The smartphone 30, in its ECG-adapted protective case 60, is held in both hands (generating a lead one, Left Arm minus Right Arm) or is placed on a person's chest to generate a modified chest lead. The ECG is measured by the acquisition electronics 11 and converted into a frequency modulated signal with a carrier or center frequency from about 6 kHz to 20 kHz, or in some embodiments from 10 kHz to 15 kHz. The frequency modulated signal is output by a miniature speaker 64 or a piezoelectric buzzer 66.

In another configuration, the ECG device 10', as shown schematically in FIG. 2, is usable as a standalone real-time ECG acquisition device. The ECG device is identical to the "case" electronics, but is present in its own housing 67 rather than being integrated into a protective case 60 for a smartphone 30. This embodiment allows for use of the device to acquire ECG data and have it communicated acoustically to a PC or other computing device for demodulation, processing, storage and display via a web application and connection.

In either configuration, the smartphone 30 utilizes its built-in microphone 25 and CPU to acquire, digitize, demodulate, process and then display the ECG data in real-time. Also, the smartphone 30 can calculate a real-time heart rate measurement and determine a cardiac rhythm diagnosis like atrial fibrillation. The smartphone 30 can utilize its 2G, 3G, Bluetooth® and WiFi connectivity to transmit the ECG and other data to a secure web server 52 for real-time distant display, storage and analysis. Also, the ECG data can be stored locally on the smartphone 30 for later review or transmission.

Figure 8:
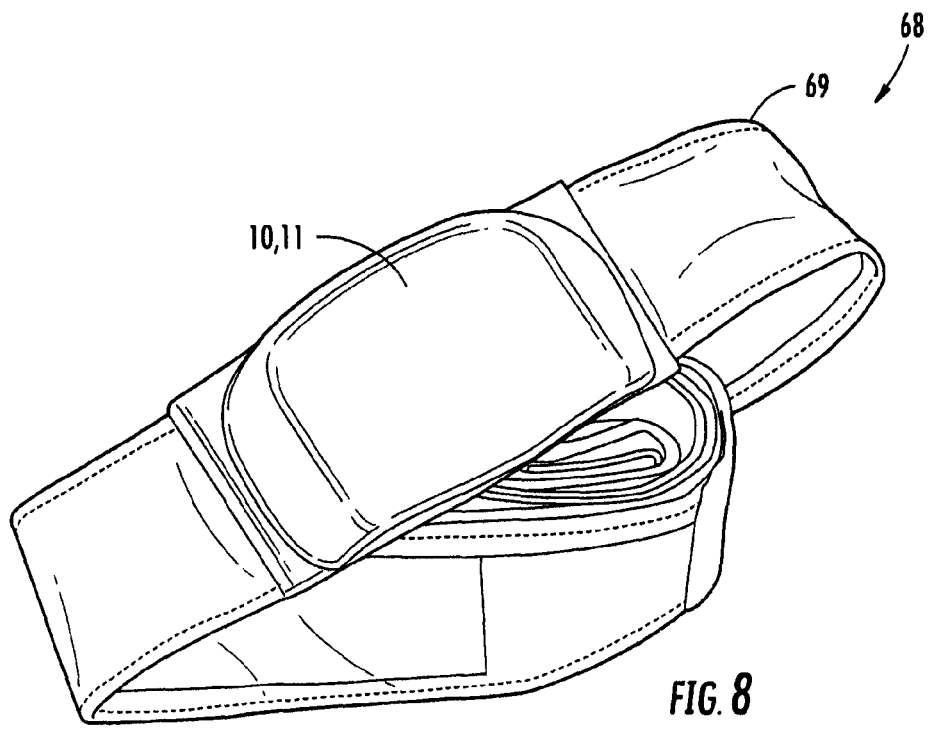
FIG. 8 is a schematic representation of an embodiment of an ECG device of the present invention included positioned within a chest strap.

In another embodiment, shown schematically in FIG. 8, the ECG device 10' is usable as a chest strap device 68 like a fitness heart rate monitor. The chest strap 69 with integrated ECG electrode assembly 18 and acquisition electronics 11 "pod" generate the frequency modulated ECG signal and send it by one of two modes to the smartphone 30. In one mode, a cable 26, as described above, plugs into the 3.5 mm headphone jack 28 on the iPhone®, Blackberry® or other smartphone 30 which provides an audio input (normally used for a headphone mic). This configuration is totally silent and immune to ambient acoustic noise. The ECG data is isolated from the smartphone 30 by an audio isolation transformer 32. In another mode, the frequency modulated audio signal is transmitted by a Bluetooth® headset chip, as described above, and the smartphone 30 receives it and performs the other processing steps. This configuration preferably makes use of mass-produced headset electronics and includes a rechargeable battery. This configuration is wireless, which provides isolation and convenience.

Software on the smartphone 30 can also combine data and signals from other sensors built into the smartphone 30 such as a GPS and accelerometer. Further processing of this data provides additional information related to the user, such as speed, location, distance, steps, cadence, body position, fall detection and energy expenditure. The raw signals from the sensors and derived information can be displayed and stored locally on the smartphone 30, as well as being transmitted to the web server 52 over an Internet connection. Software on the web server 52 provides a web browser interface for real-time or retrospective display of the signals and information received from the smartphone 30, and also includes further analysis and reporting.

Figure 9:
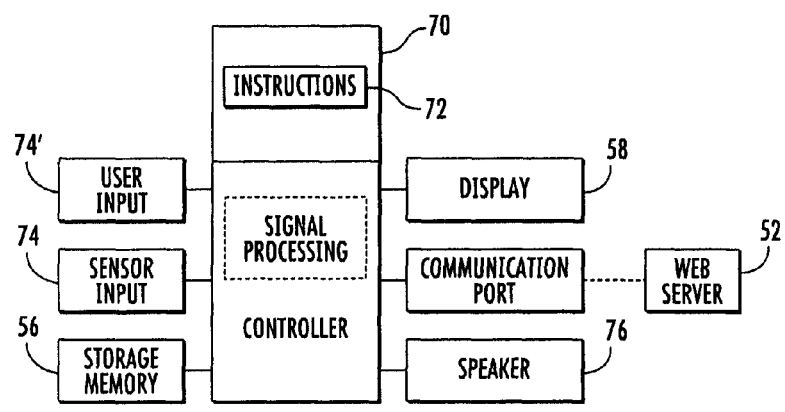
FIG. 9 is a schematic representation of a computer-readable storage medium embodiment of the present invention.

Referring now to FIG. 9, a computer-readable storage medium 56 stores a set of instructions 72, wherein the instructions 72 are capable of being executed by one or more computing devices 13. Nonlimiting examples of suitable computing devices 13 include smartphones 30, personal digital assistants (PDAs), tablet personal computers, pocket personal computers, notebook computers, desktop computers, and server computers. When executed, the one or more computing devices 13 is caused to digitize and demodulate a sensor input 74 such as a frequency modulated ECG audio signal having a carrier frequency in the range of from about 6 kHz to about 20 kHz to produce real-time demodulated digital ECG data. The instructions 72 can cause the real-time demodulated digital ECG data to display on a display screen 58 of the computing device 13.

Sensor input 74 can also include real-time information from additional sensors as well as user input 74'. For example, in embodiments wherein the computing device 13 is a smartphone 30, the input 74 can include real-time information from a GPS and/or accelerometer in the smartphone 30 in addition to the demodulated digital ECG data. User input 74' can also include spoken voice messages entered through a microphone of the computing device 13. Instructions 72 can cause the sensor and/or user input 74 and 74' to be recorded and maintained in a storage memory 56 of the computing device 13.

In one embodiment, the set of instructions 72, when executed by the one or more computing devices 13, can further cause the one or more computing devices 13 to calculate and display in real-time, a heart rate represented by the frequency modulated ECG audio signal. In addition, demodulated digital ECG data can be processed to identify the occurrence of an arrhythmia. In such designs, the storage medium 70 can include instructions 72 to cause the computing device 13 to display a warning on a display screen 58 or emit an audible alert through the speaker 76 at the occurrence of an arrhythmia.

Instructions 72 can cause the computing device 13 to store the demodulated digital ECG data in a memory 56 of the one or more computing devices 13 for later retrieval. The set of instructions 72 can further cause the one or more computing devices 13 to retrieve and transmit, upon demand, the stored demodulated digital ECG data to a web server 52 via an internet connection on the computing device 13. Recorded spoken voice messages can be stored and transmitted to the web server 52, simultaneously with the demodulated digital ECG data.

In other embodiments, the instructions 72 can cause the one or more computing devices 13 to transmit the demodulated digital ECG data, and/or voice messages, to the web server 52 in real-time.

A version of the smartphone software is packaged as a software library that can be integrated with other third party software applications. This provides a simplified and standard method for third party applications to use the ECG device 10' to obtain heart rate and other derived information without having to develop their own data acquisition, demodulation, and signal processing algorithms.

A version of the software also runs on a PC and includes demodulation, processing, storage and transmission to the web server 52. The software includes the audio acquisition, demodulation, ECG analysis, and acceleration analysis modules.

The audio acquisition module selects the appropriate audio input and samples the audio. On the iPhone®, audio is sampled and processed using the audio unit framework, which provides low latency audio acquisition and processing. The audio unit framework also allows automatic selection of the appropriate audio source, internal mic, audio jack connection, or Bluetooth® headset. The sampling rate will typically be at 44 kHz when the modulation carrier frequency is greater than 10 kHz, but for lower carrier frequencies, it may use a lower audio sampling rate. On other devices this module will use the most appropriate API's for efficient, low latency audio sampling.

The demodulation module demodulates a frequency modulated ECG audio signal, using a linear approximation and zero crossings algorithm. The demodulator allows selection of different modulation parameters to match the particular ECG device. Demodulation using zero crossings and linear approximation works well for carrier frequencies 6 kHz and lower and has the advantage that it is simple and fast.

Above 10 kHz with 44 kHz sampling, the errors from linear approximation become large, although the effect is somewhat reduced if applying a 40 Hz filter to the demodulated ECG. Application of sine or other curve fitting methods can be used to reduce the error associated with linear approximation for carrier frequencies above 10 kHz. Audio samples from the audio acquisition module are first passed through a digital band-pass filter to remove unwanted frequencies outside the modulation range. The digital band-pass filter is most effective when receiving acoustically coupled audio which can be contaminated with noise. When using a center frequency above 6 kHz, the band-pass filter is able to provide good noise immunity from voice and background ambient noise which is typically below 5 kHz. The band-pass filter stage could be eliminated to save processing power when receiving audio via a wired or Bluetooth® connection which would not be susceptible to background noise contamination. To demodulate the signal it is necessary to estimate the frequency of the audio waveform. The algorithm looks at the sign of incoming data. When the sign changes it draws a straight line between the two points and interpolates the zero value. It uses this to determine the average frequency over a 3.333 ms interval, which provides ECG data at the output sampling rate of 300 Hz.

The ECG analysis module includes algorithms that process the ECG to detect and classify beats, and provides a heart rate estimate. Beat-to-beat heart rate is calculated from the interval between beats and a more robust measurement of heart rate is calculated using median filtering of the RR intervals.

The acceleration analysis module includes algorithms that process signals from the built-in 3 axis accelerometer sensor in the smartphone 30, to derive an estimate of a person's energy expenditure, steps, cadence, and body position and to detect falls.

From the above descriptions, it is clear that the presently disclosed and claimed inventive concept(s) are well-adapted to carry out the objects and to attain the advantages mentioned herein, as well as those inherent in the presently disclosed and claimed inventive concept(s). While the presented embodiments have been described for purposes of this disclosure, it will be understood that numerous changes may be made which will readily suggest themselves to those skilled in the art and which are accomplished within the spirit of the presently disclosed and claimed inventive concept(s).

What is claimed is:

1. A non-transitory computer-readable storage medium storing a set of instructions capable of being executed by a smartphone, that when executed by the smartphone causes the smartphone to:
   digitize and demodulate a frequency modulated ECG acoustic signal having a carrier frequency in the range of from about 6 kHz to about 20 kHz received from a built-in microphone of the smartphone to produce real time demodulated digital ECG data, and
   to display on a display screen of the smartphone information about the real-time ECG signal represented by the demodulated digital ECG data.

2. The non-transitory computer-readable storage medium of claim 1, wherein the set of instructions, when executed by the smartphone, further causes the smartphone to record real-time information from a GPS and/or accelerometer in the smartphone.

3. The non-transitory computer-readable storage medium of claim 1, wherein the set of instructions, when executed by the smartphone, further causes the smartphone to record spoken voice messages simultaneously with the real-time demodulated digital ECG data.

4. The non-transitory computer-readable storage medium of claim 1, wherein the set of instructions, when executed by the smartphone, further causes the smartphone to calculate and display in real-time, a heart rate represented by the frequency modulated ECG acoustic signal.

5. The non-transitory computer-readable storage medium of claim 1, wherein the set of instructions, when executed by the smartphone, further causes the smartphone to process the demodulated digital ECG data to identify the occurrence of an arrhythmia or other abnormality.

6. The non-transitory computer-readable storage medium of claim 5, wherein the set of instructions, when executed by the smartphone, further causes the smartphone to display a warning at the occurrence of an arrhythmia or other abnormality.

7. The non-transitory computer-readable storage medium of claim 1, wherein the set of instructions, when executed by the smartphone, further causes the smartphone to store the demodulated digital ECG data in a memory of the smartphone for later retrieval.

8. The non-transitory computer-readable storage medium of claim 7, wherein the set of instructions, when executed by the smartphone, further causes the smartphone to retrieve and transmit, upon demand, the stored demodulated digital ECG data to a web server via an internet connection on the smartphone.

9. The non-transitory computer-readable storage medium of claim 8, wherein the set of instructions, when executed by the smartphone, further causes the smartphone to record spoken voice messages simultaneously with the demodulated digital ECG data, and to transmit the spoken voice messages with the demodulated digital ECG data to the web server.

10. The non-transitory computer-readable storage medium of claim 1, wherein the set of instructions, when executed by the smartphone, further causes the smartphone to transmit the demodulated digital ECG data to a web server in real-time.

11. The non-transitory computer-readable storage medium of claim 10, wherein the set of instructions, when executed by the smartphone, further causes the smartphone to record spoken voice messages simultaneously with the demodulated digital ECG data, and to transmit the spoken voice messages with the demodulated digital ECG data to the web server.

12. The non-transitory computer-readable storage medium of claim 1, wherein the set of instructions, when executed by the smartphone, further causes the smartphone to select the appropriate acoustic input and sample the frequency modulated ECG acoustic signal.

13. The non-transitory computer-readable storage medium of claim 1, wherein the set of instructions, when executed by the smartphone, further causes the smartphone to sample the frequency modulated ECG acoustic signal at a sample rate at 44 kHz.

* * * * *